United States Patent
Kobayashi et al.

(10) Patent No.: US 8,647,553 B2
(45) Date of Patent: Feb. 11, 2014

(54) STRETCH SHEET AND PROCESS OF PRODUCING THE SAME

(75) Inventors: Hideyuki Kobayashi, Tochigi (JP); Koji Kanazawa, Tochigi (JP); Akihiko Gunji, Tokyo (JP); Tetsuya Masuki, Tochigi (JP)

(73) Assignee: Kao Corporation, Tokyo (JP)

( * ) Notice: Subject to any disclaimer, the term of this patent is extended or adjusted under 35 U.S.C. 154(b) by 852 days.

(21) Appl. No.: 11/919,118

(22) PCT Filed: Apr. 25, 2006

(86) PCT No.: PCT/JP2006/308663
§ 371 (c)(1),
(2), (4) Date: Jan. 24, 2008

(87) PCT Pub. No.: WO2006/115259
PCT Pub. Date: Nov. 2, 2006

(65) Prior Publication Data
US 2009/0035527 A1    Feb. 5, 2009

(30) Foreign Application Priority Data

Apr. 25, 2005 (JP) ................. 2005-127188
Jun. 17, 2005 (JP) ................. 2005-178378

(51) Int. Cl.
*B29C 49/08* (2006.01)
*B29C 65/00* (2006.01)
*B32B 27/14* (2006.01)
*B32B 25/10* (2006.01)

(52) U.S. Cl.
USPC ............. 264/288.4; 264/173.15; 264/249; 264/257; 264/290.2; 264/291; 156/163; 156/164; 156/209; 156/229; 156/290

(58) Field of Classification Search
USPC ........ 264/288.4, 289.3, 290.2, 280, 249, 257, 264/291; 156/163, 164, 209, 229, 290; 442/394, 399, 409; 428/167, 198
See application file for complete search history.

(56) References Cited

U.S. PATENT DOCUMENTS 3,414,459 A    12/1968   Wells
4,446,189 A    5/1984    Romanek
(Continued)

FOREIGN PATENT DOCUMENTS

DE    196 47 459 A1    5/1998
EP    0556749 A1       8/1993
(Continued)

OTHER PUBLICATIONS

Chinese Office Action issued Apr. 21, 2010 in Chinese Application No. 200680014098.X.

(Continued)

*Primary Examiner* — Atul P. Khare
(74) *Attorney, Agent, or Firm* — Birch, Stewart, Kolasch & Birch, LLP

(57) ABSTRACT

In a process of producing a stretch sheet, a strip-shaped laminate sheet 10A having an elastically stretchable elastic layer 1 and substantially inelastic, inelastic fiber layers 2 and 3 partially joined to each other at bonds 4 or a strip-shaped fibrous sheet containing an elastic component and a substantially inelastic component and having embossed regions formed by embossing in parts is stretched in directions starting from the bonds 4 or the embossed regions to obtain a stretch sheet 10. The stretch sheet has raised ridges and recessed grooves extending in the direction perpendicular to the stretch direction, and the bonds 4 or the embossed regions are present in the ridges.

15 Claims, 6 Drawing Sheets

(56) References Cited

U.S. PATENT DOCUMENTS

| | | | |
|---|---|---|---|
| 5,143,679 A * | 9/1992 | Weber et al. | 264/288.8 |
| 5,156,793 A | 10/1992 | Buell et al. | |
| 5,167,897 A | 12/1992 | Weber et al. | |
| 5,591,155 A | 1/1997 | Nishikawa et al. | |
| 5,683,787 A | 11/1997 | Boich et al. | |
| 5,691,034 A | 11/1997 | Krueger et al. | |
| 6,258,308 B1 * | 7/2001 | Brady et al. | 264/210.2 |
| 6,878,433 B2 * | 4/2005 | Curro et al. | 428/198 |
| 6,878,647 B1 | 4/2005 | Rezai et al. | |
| 2002/0068150 A1 | 6/2002 | Taneichi et al. | |
| 2003/0120240 A1 | 6/2003 | Buell et al. | |
| 2004/0067710 A1 | 4/2004 | Tsujiyama et al. | |
| 2006/0121812 A1 | 6/2006 | Suzuki et al. | |

FOREIGN PATENT DOCUMENTS

| | | |
|---|---|---|
| JP | 63-81887 U | 5/1988 |
| JP | 3-64157 B2 | 10/1991 |
| JP | 6-133998 A | 5/1994 |
| JP | 9-117982 A | 5/1997 |
| JP | 2002-69815 A1 | 3/2002 |
| JP | 2002-187228 A | 7/2002 |
| JP | 2004-166832 A | 6/2004 |
| JP | 2004-244791 A | 9/2004 |
| JP | 2005-89870 A | 4/2005 |
| WO | WO 00/27328 A1 | 5/2000 |
| WO | WO 00/37000 A1 | 6/2000 |
| WO | WO 00/37725 A1 | 6/2000 |
| WO | WO-2004/038085 A2 | 5/2004 |

OTHER PUBLICATIONS

The extended European Search Report for EP Appl. No. 06732323, dated Apr. 27, 2009.

International Preliminary Report on Patentability issued Oct. 30, 2007, in PCT International Application No. PCT/JP2006/308663.

Office Action issued Sep. 14, 2010, in Japanese Patent Application No. 2006-119842 (with English translation).

Office Action Issued Sep. 28, 2010, in Japanese Patent Application No. 2006-121149 (with English translation).

Chinese Office Action for Chinese Patent Application No. 200680014098.X dated Feb. 28, 2012.

European Communication of a Notice of Opposition, dated Jul. 10, 2012, for European Application No. 06732323.8.

* cited by examiner

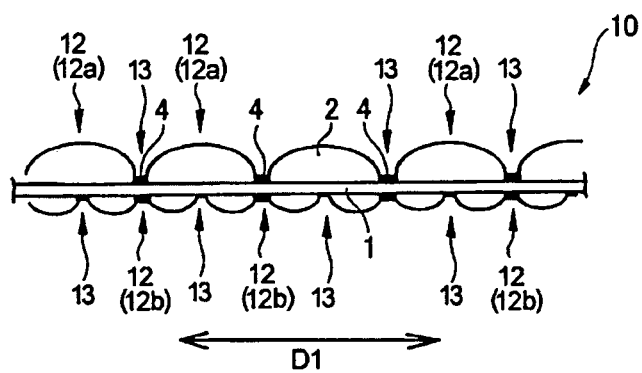
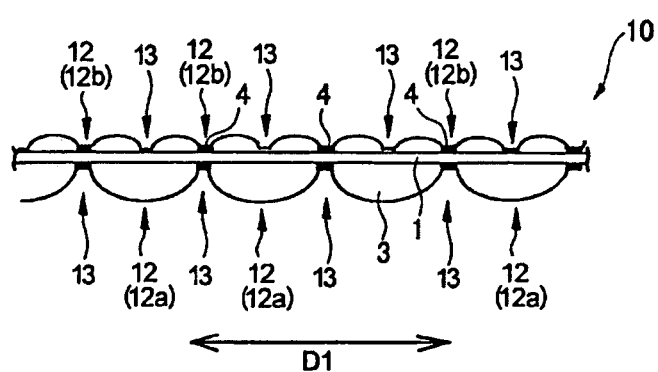

STRETCH SHEET AND PROCESS OF PRODUCING THE SAME

TECHNICAL FIELD

The present invention relates to a process of producing a stretch sheet, a method of stretching a laminate sheet or a fibrous sheet, and a stretch sheet.

BACKGROUND ART

A process of producing a stretch sheet is known, in which a sheet material having elastic stretchability and a substantially inelastic sheet material are joined together in parts and then stretched. For example, EP 0556749A1 discloses a process of producing a stretch composite sheet, comprising joining an elastic sheet in its relaxed state and a base sheet having extensibility equal to that of the elastic sheet but non-recoverable continuously in the longitudinal direction (MD) and discontinuously in the width direction (CD) to make an elastic composite sheet, stretching the elastic composite sheet to cause the base sheet to be deformed permanently within a limit that does not cause the base sheet to cut or break, and releasing the composite sheet from the stretched state.

However, conventional processes of producing a stretch sheet as described above are disadvantageous in that the two sheet materials joined in parts tend to separate on stretching, depending on the degree of stretching. It would follow that the resulting stretch sheet has insufficient tensile strength or easily fuzzes or breaks to have a poor hand or appearance. Such inconvenience could be averted by, for example, lowering the stretch ratio, which makes it difficult to produce a highly stretchable sheet.

DISCLOSURE OF THE INVENTION

The present invention provides, in its first aspect, a process of producing a stretch sheet, in which a laminate sheet having an elastically stretchable elastic layer and a substantially inelastic fiber layer joined in parts to the elastic layer at bonds is stretched in directions starting from the bonds.

The present invention also provides, in its second aspect, a process of producing a stretch sheet, in which a fibrous sheet containing an elastic component and a substantially inelastic component and having embossed regions formed by embossing in parts is stretched in directions starting from the embossed regions.

The present invention also provides a process of producing a stretch sheet. The process includes the steps of providing a strip-shaped laminate sheet having an elastically stretchable elastic layer and a substantially inelastic fiber layer partially joined to each other at bonds or a strip-shaped embossed fibrous sheet containing an elastic component and a substantially inelastic component and having embossed regions in parts and stretching the laminate sheet or the fibrous sheet in the width direction between a pair of corrugated rolls. The corrugated rolls each have axially alternating large-diameter segments and small-diameter segments and are in a meshing engagement with each other such that the large-diameter segments of one of the corrugated rolls fit with clearance between adjacent large-diameter segments of the other corrugated roll. The laminate sheet or the embossed fibrous sheet is introduced between the pair of corrugated rolls such that the positions of the bonds or the embossed regions in the width direction coincide with the positions of the large diameter segments of the corrugated rolls.

The present invention also provides a method of stretching a laminate sheet characterized in that a laminate sheet having an elastically stretchable elastic layer and a substantially inelastic fiber layer partially joined to each other at bonds is stretched in directions starting from the bonds.

The present invention also provides a stretch sheet having an elastically stretchable elastic layer and a substantially inelastic fiber layer partially joined to each other at bonds arranged along the stretch direction of the stretch sheet. The stretch sheet has raised ridges and recessed grooves on at least one side thereof. The raised ridges and recessed grooves alternate in the stretch direction and extend in the direction perpendicular to the stretch direction. The bonds are located at least in the raised ridges.

The present invention also provides a stretch sheet containing an elastic component and a substantially inelastic component and having embossed regions arranged in the stretch direction of the stretch sheet. The stretch sheet has raised ridges and recessed grooves on at least one side thereof. The raised ridges and recessed grooves alternate in the stretch direction and extend in the direction perpendicular to the stretch direction. The bonds are located at least in the raised ridges.

BRIEF DESCRIPTION OF THE DRAWING

FIG. 3(a) is a cross-section taken along line I-I of FIG. 2; FIG. 3(b) is a cross-section corresponding to FIG. 3(a), in which the laminate sheet has been deformed (stretched) between corrugated rolls; FIG. 3(c) is a cross-section taken along line II-II of FIG. 2; and FIG. 3(d) is a cross-section corresponding to FIG. 3(c), in which the laminate sheet has been deformed (stretched) between corrugated rolls.

FIG. 4(a) and FIG. 4(b) are each a schematic illustration of a stretch nonwoven fabric (stretch sheet) obtained by stretching the laminate sheet of FIG. 2 in the CD. Specifically, FIG. 4(a) is a cross-section corresponding to that taken along line I-I of FIG. 2, and FIG. 4(b) is a cross-section corresponding to that taken along line II-II of FIG. 2.

FIG. 5(a) is a schematic plan of the inelastic fiber layer side of a stretch nonwoven fabric (stretch sheet); and FIG. 5(b) is a cross-section taken along line III-III of FIG. 5(a).

DETAILED DESCRIPTION OF THE INVENTION

The present invention will be described based on its preferred embodiments with reference to the accompanying drawings.

Figure 3A:
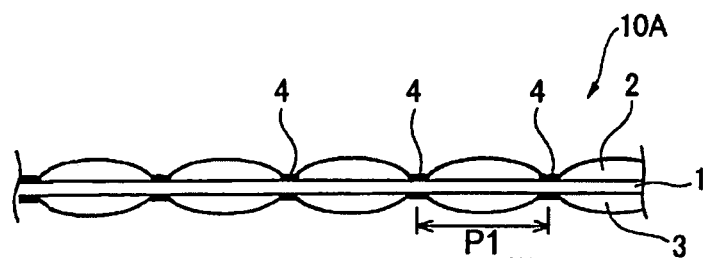
FIGS. 3(a) to 3(d) each represent a schematic cross-section of the laminate sheet of FIG. 2, taken along the CD. Specifically.

In a first embodiment of the invention, a laminate sheet 10A is subjected to a stretching operation. As illustrated in FIGS. 3(a) and 3(c), the laminate sheet 10A is a stack of a first fiber layer (elastic layer) 1 having elastic stretchability and a substantially inelastic, second and third fiber layers (inelastic fiber layers) 2 and 3 on the respective sides of the first fiber layer 1. The three fiber layers are partially joined to one another in a regular pattern.

Figure 1:
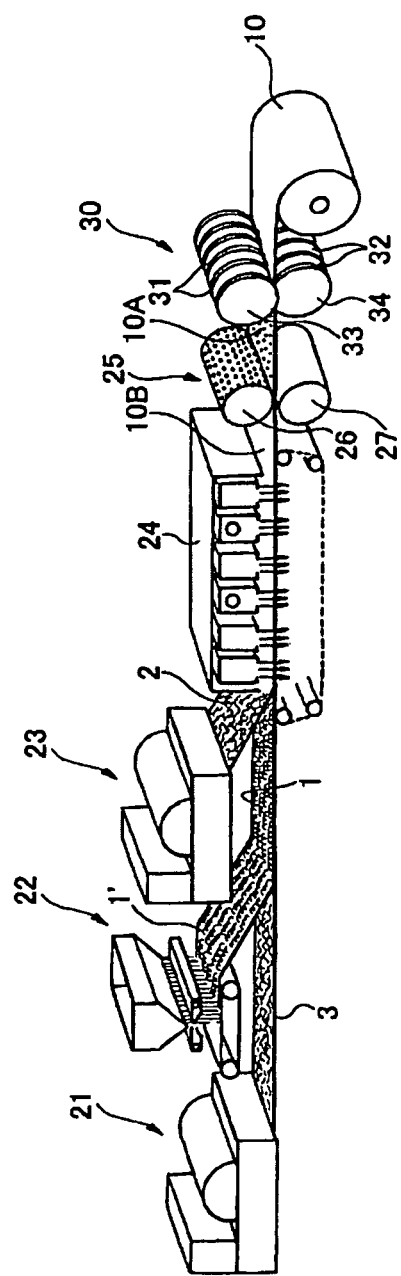
FIG. 1 is a schematic illustration of apparatus for producing a stretch sheet that can be used in a preferred embodiment of a process of producing a stretch sheet according to the present invention.

The laminate sheet 10A used in the present embodiment is prepared, for example, as illustrated in FIG. 1. A fiber web (third fiber layer) 3 is continuously fed from a first carding machine 21 in one direction (MD). Elastic fibers 1' formed in the fiber forming unit 22 are fed on the fiber web 3 to form a layer (first fiber layer) 1 of the elastic fibers 1' in a continuous manner. A fiber web (second fiber layer) 2 fed from a second carding machine 23 is continuously fed on the first fiber layer 1. The resulting stack of three layers is subjected to a hot air treatment in a through-air system drier 24. The hot air treated laminate sheet 10B is heat embossed through an embossing unit 25 including an embossing roll 26 having embossing projections regularly arranged on its peripheral surface and an anvil roll 27 facing to the embossing roll 26. There is thus obtained the laminate sheet 10A having bonds 4 in a regular pattern as illustrated in FIGS. 3(a) and 3(c).

In the process described above, the hot air treatment in the drier 24 is for causing the elastic fibers and the inelastic fibers to be fusion bonded or to mutually enter the adjoining fiber layer. The hot air treatment may be omitted.

A preferred structure of the laminate sheet 10A will be described.

The first fiber layer (elastic layer) 1 has the capability of extending under tension and contracting when released from the tension. When it is 100% elongated in at least one direction parallel to its plane and then contracted, the residual strain is preferably 20% or less, more preferably 10% or less. It is desirable that the first fiber layer 1 has the recited residual strain in at least one of the MD and CD, particularly preferably in both the MD and CD. The maximum elongation is preferably 30% to 500%, more preferably 300% to 500%.

The first fiber layer (elastic layer) 1 preferably contains elastic fibers made from an elastic material. Elastic materials include thermoplastic elastomers, rubber, and ethylene-propylene copolymers. Thermoplastic elastomers are preferred of them; for they are relatively easily formed into elastic fibers. Examples of the thermoplastic elastomers include polyurethane elastomers, styrene elastomers (e.g., SBS, SIS, SEBS, and SEPS), olefin elastomers (e.g., ethylene, propylene or butene copolymers), vinyl chloride elastomers, and polyester elastomers. These elastomers may be used either individually or in combination of two or more thereof.

The proportion of the elastic fibers made from an elastic material in the first fiber layer 1 is preferably 50% to 100% by weight, more preferably 75% to 100% by weight. The elastic resin of the first fiber layer may contain an inelastic resin, e.g., polyethylene, polypropylene, polyester (e.g., PET or PBT) or nylon, an organic or inorganic pigment, and various additives (e.g., an antioxidant or a plasticizer). The first fiber layer may contain inelastic fibers and an organic or inorganic pigment.

The elastic layer may be a film or a net instead of the fiber layer. The film or net can be made from the above enumerated elastic materials.

The second and third fiber layers (inelastic fiber layers) 2 and 3 are extensible but substantially inelastic. The term "extensible" as used herein is intended to include not only a fiber layer whose constituent fibers per se are extensible but also a fiber layer whose constituent fibers are not per se extensible but which shows extensibility as a result of debonding of constituent fibers that have been fusion bonded at their intersections, change of three-dimensional structures formed of a plurality of constituent fibers fusion-boded to one another, or breaks of the constituent fibers.

Fibers constituting the inelastic fiber layers include those made of polyethylene, polypropylene, polyester (e.g., PET or PBT), nylon, or a biodegradable resin (e.g., polylactic acid). The fibers constituting the inelastic fiber layers may be staple fibers or continuous fibers and hydrophilic or water repellent. Sheath-core conjugate fibers, dividual fibers, modified cross-section fibers, crimped fibers, and heat shrunken fibers are also useful. These fibers may be used either individually or in combination of two or more thereof. Although staple fibers are apt to cause fuzzing when stretched, the process of the present embodiment hardly induce destruction of the bonds even where staple fibers are used. Therefore, using staple fibers is preferred as providing a stretch sheet having high strength, resistance to fuzzing, and a good feel to the touch.

Figure 2:
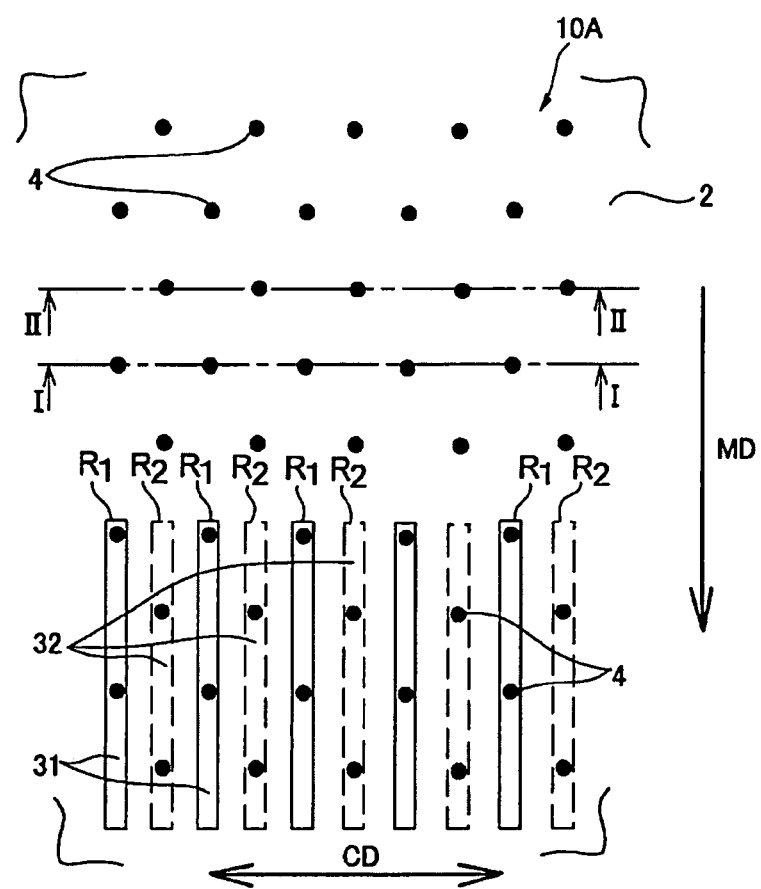
FIG. 2 is a plan of an example of a laminate sheet to be stretched in the present invention.
Figure 3B:
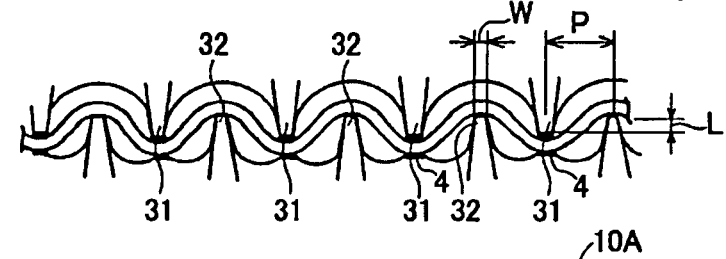
Figure 3C:
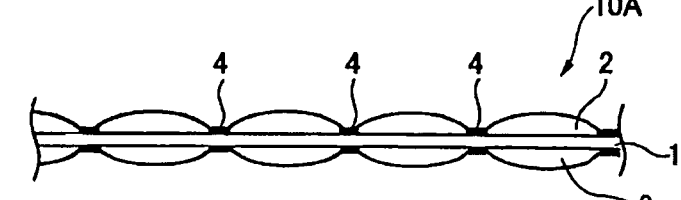

The bonds 4 are preferably arranged discretely in both the machine direction (MD) and the direction perpendicular to the MD (i.e., CD) of the laminate sheet 10A as illustrated in FIGS. 2, 3(a), and 3(b). It is preferred that the second fiber layer and/or the third fiber layer have recesses at the bonds 4 and protrusions at other sites than the bonds 4 so as to provide a stretch nonwoven fabric (stretch sheet) with a pleasant feel to the touch.

In the first embodiment, the three-layered laminate sheet 10A is subjected to the step of stretching.

In the first embodiment, the laminate sheet 10A is stretched in the direction perpendicular to the running direction, i.e., the CD by use of a stretching unit 30 having a pair of corrugated rolls 33 and 34. The corrugated rolls 33 and 34 each consist of axially alternating large-diameter segments 31 and 32, respectively, and small-diameter segments (not shown).

The stretching unit 30 has a known vertical displacement mechanism for vertically displacing the axis of either one of or both of the corrugated rolls 33 and 34 to adjust the clearance between the rolls 33 and 34.

Figure 3D:
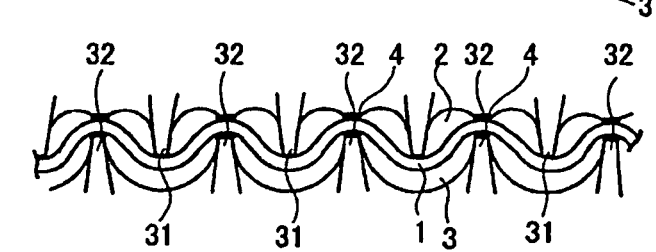

As illustrated in FIGS. 1, 3(b), and 3(d), the corrugated rolls 33 and 34 are configured such that the large-diameter segments 31 of the corrugated roll 33 fit with clearance into the recesses between adjacent large-diameter segments 32 of the other corrugated roll 34 and that the large-diameter segments 32 of the corrugated roll 34 fit with clearance into the recesses between adjacent large-diameter segments 31 of the other corrugated roll 33. The laminate sheet 10A is introduced into the nip between the so configured rolls 33 and 34 to be stretched.

In the stretching step, the positions of the bonds 4 of the laminate sheet 10A in the width direction are coincident with those of the large-diameter segments 31 and 32 of the respective corrugated rolls 33 and 34 as illustrated in FIGS. 3(a) through 3(d). Specifically, as illustrated in FIG. 2, the laminate sheet 10A has straight lines of bonds (hereinafter "bond lines" (10 bond lines in FIG. 2) parallel to the MD, each line having the bonds 4 spacedly aligned in the MD. The positions of the large-diameter segments 31 of the corrugated roll 33 are coincident with the positions of the bonds 4 in every other bond line starting with the first bond line to the left in FIG. 2, designated R1. The positions of the large-diameter segments 32 of the other corrugated roll 34 are coincident with the positions of the bonds 4 in every other bond line starting with the second bond line to the left, designated R2. The regions indicated by numerals 31 and 32 in FIG. 2 are the regions of the laminate sheet 10A that are to come into contact with the top face of the large-diameter segments 31 and 32 of the rolls 33 and 34, respectively, at a point of time while the sheet 10A is passing between the corrugated rolls 33 and 34.

During the passage of the laminate sheet 10A between the corrugated rolls 33 and 34, the bonds 4 come into contact with the large-diameter segments (31 or 32) of either of the rolls 33 and 34, while the regions of the laminate sheet 10A between the large-diameter segments (the regions that do not come into contact with the large-diameter segments) are positively stretched as illustrated in FIGS. 3(b) and 3(d). Therefore, the laminate sheet 10A is stretched in opposite directions starting from every bond 4. In other words, the laminate sheet 10A is efficiently stretched in the regions other than the bonds 4 without being accompanied by breaks or separation at the bonds 4. This stretching operation elongates the second and third fiber layers (inelastic fiber layers) 2 and 3 to cause non-recoverable extension (deformation) that is not recovered even after the fibrous sheet 10A contracts as a whole. Being so deformed, the second and third fiber layers (inelastic fiber layers) 2 and 3 exhibit greatly lessened action to interfere with free expansion and contraction of the elastic fiber layer. Thus, the process of the present embodiment efficiently produces a stretch nonwoven fabric (stretch sheet) exhibiting high stretchability, a soft feel to the touch, high strength resistant to break, and a good appearance with little fuzzing.

The non-recoverable extension that occurs in the second and third fiber layers (inelastic fiber layers) 2 and 3 is exemplified by the above-described deformations resulting from non-recoverable extension of constituent fibers, debonding of constituent fibers that have been fusion bonded at their intersections, change of three-dimensional structures formed of a plurality of constituent fibers fusion-boded to one another, or breaks of the constituent fibers. In order to obtain a stretch nonwoven fabric (stretch sheet) that feels comfortable to the touch, it is preferred that the non-recoverable extension is a deformation resulting from debonding of the fusion bonded fibers or partial breaks of the fibers to an extent that does not cause noticeable fuzzing.

FIGS. 4(a) and 4(b) are each a cross-section of the stretch nonwoven fabric 10 obtained by the process of the first embodiment. FIG. 4(a) is a cross-section corresponding to that taken along line I-I of FIG. 2, and FIG. 4(b) is a cross-section corresponding to that taken along line II-II of FIG. 2.

Figure 5A:
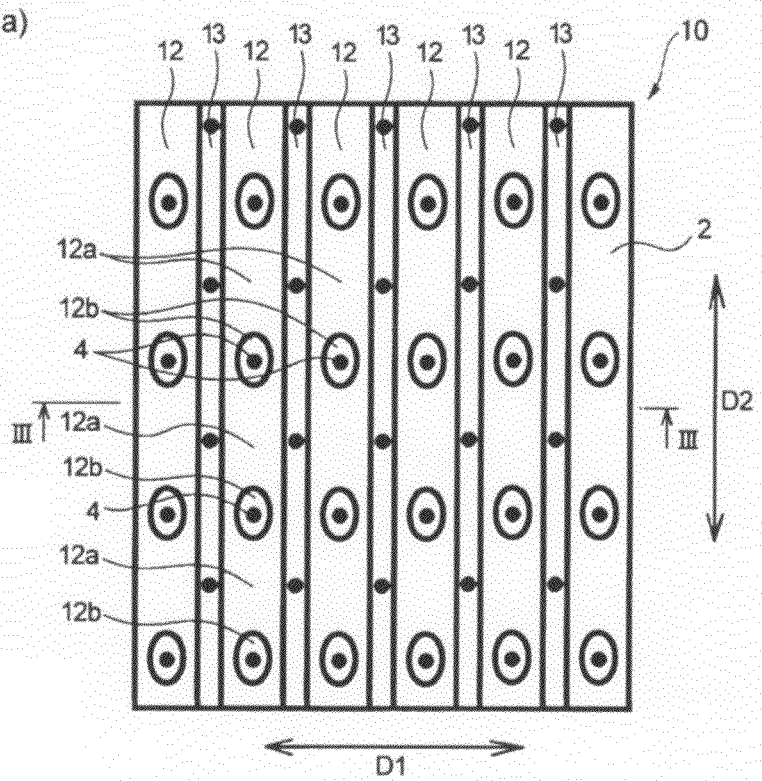
FIG. 5(a) and FIG. 5(b) each illustrate a preferred embodiment of a stretch sheet according to the present invention. Specifically.
Figure 5B:
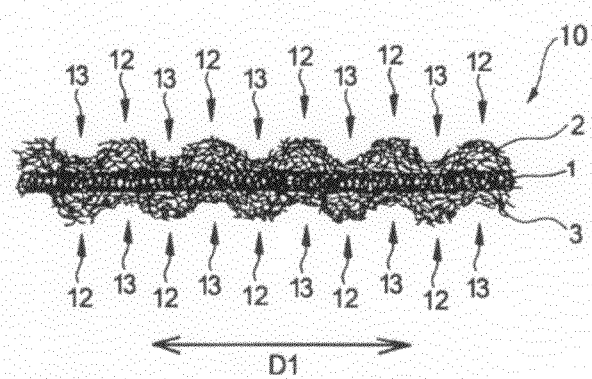

FIG. 5(a) is a schematic plan of the inelastic fiber layer side of the stretch nonwoven fabric (stretch sheet) 10, and FIG. 5(b) is a cross-section taken along line III-III of FIG. 5(a).

As illustrated in FIG. 5(b), the stretch nonwoven fabric 10 has a laminate structure including an elastically stretchable first fiber layer (elastic layer) 1 and substantially inelastic second and third fiber layers (inelastic fiber layers) 2 and 3 on the respective sides of the first fiber layer 1. The stretch nonwoven fabric (stretch sheet) 10 has bonds 4 at which the second fiber layer 2, the first fiber layer 1, and the third fiber layer 3 are united in their thickness direction arranged in the stretch direction (direction D1) thereof.

As used herein the term "stretch direction" means the direction in which the laminate sheet (having an elastic layer and an inelastic layer partially bonded to each other) or the fibrous sheet (containing an elastic component and an inelastic component and having embossed regions in parts) is stretched to obtain the stretch sheet. The stretch direction is parallel to the plane of the sheet. The stretch direction is equal to the extensible-contractible direction of the stretch sheet. When the stretch history of a stretch sheet is unknown, the direction of maximum expansion and contraction of the stretch sheet is regarded as the stretch direction. When a stretch sheet is stretchable in only one direction parallel to the plane of the sheet, this direction is taken as the direction of maximum expansion and contraction. When a stretch sheet is stretchable in a plurality of directions parallel to the plane of the sheet, the direction of maximum expansion and contraction is the direction perpendicular to the direction showing the least elongation at the maximum strength in a tensile test.

The stretch nonwoven fabric 10 of the present embodiment is obtained by stretching the laminate sheet 10A in the width direction (i.e., the CD). The stretch nonwoven fabric 10 is most stretchable in the same direction as the width direction of the laminate sheet 10A. Accordingly, the same direction as the width direction of the laminate sheet 10A, that is, the CD perpendicular to the machine direction (MD) during the production is the stretch direction and the direction of maximum expansion and contraction.

As illustrated in FIGS. 4(a), 4(b), 5(a), and 5(b), the stretch nonwoven fabric 10 has raised ridges 12 and recessed grooves 13 on both sides thereof. The raised ridges 12 and the recessed grooves 13 alternate in the stretch direction (D1) and extend in the direction D2 that is perpendicular to the stretch direction D1 on each side of the stretch nonwoven fabric 10.

The raised ridges 12 and the recessed grooves 13 alternate in the stretch direction on each side of the stretch nonwoven fabric 10. Therefore, the stretch nonwoven fabric 10 microscopically assumes a waving profile in a cross-sectional view. The waving profile is the result of stretching in the production of the stretch nonwoven fabric 10. The waving profile is the result of imparting stretchability to the stretch nonwoven fabric 10. To have a waving profile does not adversely affect the hand of the nonwoven fabric 10 but is rather beneficial for providing softer and more agreeable nonwoven fabric.

As illustrated in FIG. 5(a), the raised ridges 12 on each side of the stretch nonwoven fabric 10 generally extend in the direction D2 perpendicular to the stretch direction. Along the longitudinal direction of the raised ridge 12 are spacedly formed the bonds 4. The bonds 4 are located at nearly the midpoint of the width of the raised ridge 12.

The raised ridge 12 is highest at nearly the middle portion between every adjacent bonds 4 and is relatively lower at and around the bonds 4, forming small recesses 12b at and around the bonds 4.

Along the grooves 13 are also spacedly formed the bonds 4. The bonds 4 are located at a nearly midpoint of the width of the grooves 13.

The presence of the bonds 4 in the raised ridges 12 prevents fuzzing.

It is only necessary that the bonds are formed in the raised ridges when seen from either side of the stretch sheet. The bonds formed in the recessed grooves when seen from one side of the stretch sheet are regarded to be in raised ridges only if the grooves correspond to raised ridges on the opposite side.

The stretch nonwoven fabric 10 of the present embodiment is stretchable in its regions between every bond line $R_1$ located in every ridge 12 and every adjacent bond line $R_2$ located in an adjacent groove 13. The stretch nonwoven fabric 10 is substantially unstretchable in the bond lines $R_1$ located in the ridges 12 and the bond lines $R_2$ located in the grooves 13, or the degree of stretch, if any, in these bond lines is lower than in the regions between the bond lines. Each bond line $R_1$ of the ridge 12 is a continuous strip overlapping the bonds 4 of the ridge 12 and having practically the same width as the individual bonds 4. Each bond line $R_2$ of the groove 13 is a continuous strip overlapping the bonds 4 of the groove 13 and having practically the same width as the individual bonds 4.

The top face of each large-diameter segment of the corrugated rolls is preferably not sharply pointed so as not to damage the laminate sheet 10A (or a fibrous sheet in the second aspect of the invention). It is preferably a flat face having a certain width as illustrated in FIGS. 3(b) and 3(d). The top face width W of the large-diameter segments (see FIG. 3(b)) is preferably 0.3 to 1 mm and is preferably 0.7 to 2 times, more preferably 0.9 to 1.3 times, the size of the bonds 4 in the CD.

The pitch P of the facing large-diameter segments of the two corrugated rolls in meshing engagement (see FIG. 3(b)) is preferably 0.7 to 2.5 mm. The pitch P is preferably 1.2 to 5 times, more preferably 2 to 3 times, the size of the bonds 4 in the CD. With that configurational design, a cloth-like appearance and a good feel to the touch can be obtained. Although the pitch P1 of the bonds 4 in the CD (the pitch of bond lines R1 or R2 in the CD, see FIG. 3(a)) is basically double the pitch P of the facing large-diameter segments for positional coincidence, positional coincidence will be obtained as long as the pitch P1 falls within the range of from 1.7 to 2.3 times the pitch P taking into consideration the elongation and neck-in of the laminate sheet 10A in the CD. By setting the ratio of the pitch P1 of the bonds 4 to the pitch P of the large-diameter segments within the recited range, it is possible to stably match the large-diameter segments with the bond lines of the laminate sheet 10A. As a result, the regions of the laminate sheet 10A that run without contact with the large diameter segments are stretched at a higher ratio than the regions that pass in contact with the large diameter segments. Since the stretch ratio of the regions of the laminate sheet 10A that pass in contact with the large diameter segments is lower than those which pass without contact with the large diameter segments, the positions of the regions having the bond lines hardly deviate from the positions of the large diameter segments in the stretch direction.

Methods for stretching the laminate sheet 10A in directions starting from the bonds 4 between the elastic layer and the inelastic layer(s) include not only the above-described method in which the large-diameter segments 31 and 32 of corrugated rolls are matched with the bonds 4 so that the regions between the large-diameter segments 31 and 32 are stretched positively but also the method described in JP 6-133998A.

While, in the process illustrated in FIGS. 3(a) through 3(d), the laminate sheet 10A is stretched without being nipped between the large-diameter segments of one of the corrugated rolls and the small-diameter segments of the other corrugated roll, the clearance between the two corrugated rolls may be decreased so that the fibrous sheet 10A may be stretched as nipped between them.

By the above described stretching step, the thickness of the laminate sheet 10A preferably increases to 1.1 to 3 times, more preferably 1.3 to 2 times, the thickness before the stretching. The fibers of the inelastic fiber layers 2 and 3 extend and become finer as a result of plastic deformation. At the same time, the inelastic fiber layers 2 and 3 become bulkier to provide better feel to the touch and improved cushioning.

It is advantageous for the laminate sheet 10A before being stretched to have a lesser thickness for saving the space for transportation and storage of the stock roll.

It is preferred that the stretching step be such that the bending stiffness of the laminate sheet 10A is reduced to 30% to 80%, more preferably 40% to 70%, of that before the stretching operation thereby to provide a soft and drapable nonwoven fabric. It is preferred for the laminate sheet 10A before being stretched to have a high bending stiffness so that the laminate sheet 10A may be prevented from wrinkling during transfer and stretching operation.

The thickness and bending stiffness of the laminate sheet 10A before and after the stretching operation can be controlled by the elongation of the fibers used to make the inelastic fiber layers 2 and 3, the embossing pattern of the embossing roll, the pitch and top face width of the large-diameter segments of the corrugated rolls 33 and 34, and the depth of engagement between the corrugated rolls 33 and 34.

When at least 40%, more preferably 70% or more, in number, of the bonds 4 are starting points of the stretch in the stretching operation, the resulting stretch sheet has high stretchability, a good hand and appearance, a high maximum strength, high bulkiness, and good cushioning properties.

In a second embodiment of the present invention, a stretching operation is applied to a single layer fibrous sheet containing an elastic component and a substantially inelastic component and having embossed regions in parts.

Examples of the fibrous sheet according to the second embodiment include (1) a fiber web or a nonwoven fabric prepared by various processes which are made of sheath-core conjugate fibers having an elastic component as a core and a substantially inelastic component as a sheath or side-by-side conjugate fibers or dividual fibers having an elastic component and a substantially inelastic component and which are embossed to form embossed regions in the same pattern as in the first embodiment and (2) a fiber web or a nonwoven fabric prepared by various processes which are made of a blend of elastic fibers and inelastic fibers and embossed to form embossed regions in the same pattern as in the first embodiment. Specific examples of the fibrous sheet include a carded fiber web, a spun-bonded or melt-blown fiber web, a hydroentangled fiber web or a needle-punched fiber web each embossed with a heat roll to have a large number of fusion bonds in a discrete dot pattern in a plan view.

The elastic component is exemplified by the above-described materials constituting the elastic fibers. The substantially inelastic component is exemplified by the above described materials constituting the inelastic fibers.

In the second embodiment, the fibrous sheet is stretched in directions starting from the embossed regions in the same manner as in the first embodiment, in which the laminate sheet is stretched in directions starting from the bonds. In the first embodiment, the three-layered laminate sheet 10A is introduced into the nip of the corrugated rolls with the positions of the bonds 4 in the width direction coincide with the positions of the large diameter segments of the rolls. Instead, the single layer fibrous sheet is introduced into the nip of the corrugated rolls with the embossed regions coincide with the positions of the large diameter segments of the rolls.

By using the embossed regions as starting points of stretching, the fibrous sheet is efficiently stretched in the regions other than the embossed regions without being accompanied by breaks at the embossed regions.

Similarly to the stretch nonwoven fabric 10, the stretch sheet has raised ridges and recessed grooves on both sides thereof which alternate in the stretch direction and extend in the direction perpendicular to the stretch direction. The embossed regions are located in the ridges and grooves. The stretching of the single layer fibrous sheet is preferably carried out under the same conditions as in stretching the laminate sheet 10A.

The stretch nonwoven fabric (stretch sheet) obtained by the process of the present invention is useful in various applications such as clothing, cleaning sheets, car interiors, furniture, and bedding. It is especially useful as a constituent material of absorbent articles such as sanitary napkins and disposable diapers. For example, it is useful as a sheet for elasticizing a waist portion, a below-waist portion, a leg opening portion, etc. of a disposable diaper. It is also useful as a sheet forming stretchable wings of a sanitary napkin. It is applicable to any portion that is designed to be elasticized. In applying a two- or three-layered stretch nonwoven fabric composed of an elastic layer and an inelastic fiber layer(s) to a site that is to come into contact with the wearer's skin, the stretch nonwoven fabric is preferably used with its inelastic fiber layer side being to face the wearer's skin to give a wearer stickiness-free comfort. The method of stretching a laminate sheet or a fibrous sheet according to the present invention is preferably applied to the production of stretch nonwoven fabric (stretch sheet) as in the aforementioned embodiments. The method is useful in other applications as well.

The present invention is not limited to the above embodiments. For instance, while the laminate sheet 10A used in the first embodiment has a three layer structure, a laminate sheet having the inelastic layer on either side of the first fiber layer (elastic layer) is useful as well. While the bonds in the first aspect of the invention and the embossed regions in the second aspect of the invention are arranged in a staggered pattern, they may be arranged in other patterns. The bonds of the laminate sheet or the embossed regions of the fibrous sheet may be arranged in various patterns. For example, in the pattern shown in FIG. 2, the longitudinal positions of the bonds in a bond line extending in the MD may be the same as those in an adjacent bond line, or the pattern may consist of three or more kinds of bond lines extending in the MD and different in longitudinal positions of the bonds. The stretch sheet that stretches in the CD may have its bonds connected in the MD. The stretch sheet that stretches in the MD may have its bonds connected in the CD. As long as the bond lines coincide with the large diameter segments of the corrugated rolls, the sheet may additionally have bonds in regions between the large diameter segments.

The bonds in the first aspect of the invention may be formed by not only heat embossing but other means such as ultrasonic embossing, high frequency embossing or an adhesive. Likewise, the embossed regions in the second aspect of the invention may be formed by not only heat embossing but other embossing techniques such as ultrasonic embossing or high frequency embossing. Shapes of the bonds and embossed regions in the plan view include circular, elliptic, triangular, and rectangular. The bonds or embossed regions may have two or more of these shapes in combination.

While in the foregoing embodiments the laminate sheet or the fibrous sheet is stretched in the CD, the stretch direction may be the MD.

Figure 6:
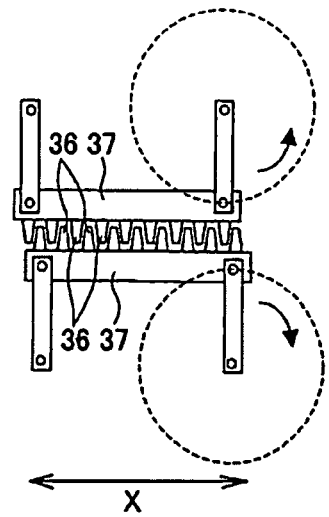
FIG. 6 illustrates an example of a stretching unit for stretching a laminate sheet or a fibrous sheet in the MD.
Figure 7:
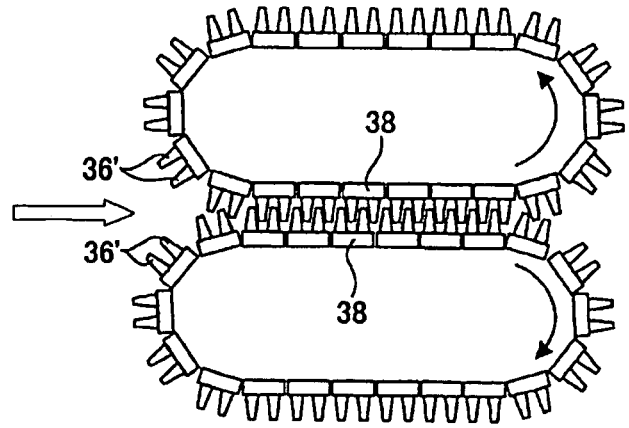
FIG. 7 illustrates another example of a stretching unit for stretching a laminate sheet or a fibrous sheet in the MD.
Figure 8:
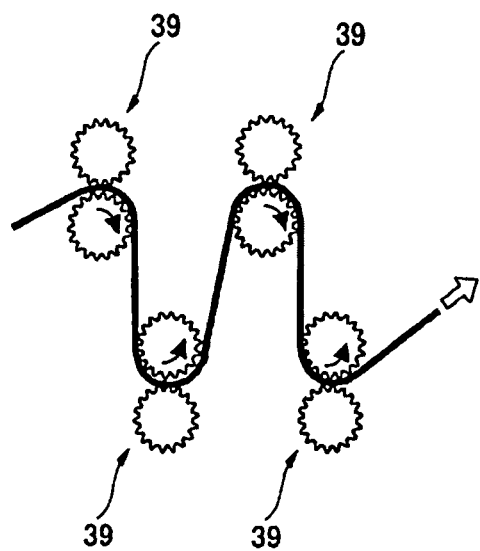
FIG. 8 illustrates still another example of a stretching unit for stretching a laminate sheet or a fibrous sheet in the MD.

For example, stretching units illustrated in FIGS. 6 to 8 can be used. The unit shown in FIG. 6 has a pair of corrugated plates 37 having a number of ridges 36 extending in the direction perpendicular to direction X on their respective facing sides and is configured to have the distance between the corrugated plates varied by a cam mechanism. While the corrugated plates are vertically separated apart, the laminate sheet or fibrous sheet is set therebetween with its MD coincide with the direction X and the positions of the bonds of the laminate sheet or the embossed regions of the fibrous sheet coincide with the positions of the ridges, followed by displacing the corrugated plates into a matched engagement as shown in FIG. 6 whereby the laminate sheet or fibrous sheet is stretched.

The stretching unit illustrated in FIG. 7 has a pair of caterpillars 38 each having ridges 36' like the ridges of the stretching unit shown in FIG. 6. The laminate sheet or fibrous sheet is introduced between the caterpillars in the direction indicated by the arrow in FIG. 7 and stretched in the MD continuously.

The stretching unit illustrated in FIG. 8 is a multi-gear system having a plurality of pairs of corrugated rolls (gears) as stretching sites 39. The stretch ratio at each pair of corrugated rolls increases in the upstream direction.

The laminate sheet or fibrous sheet can be stretched in the MD starting at its bonds or embossed regions by the use of the stretching units illustrated in FIGS. 6 to 8.

A laminate sheet having an elastic layer and a substantially inelastic layer joined all over to each other and additionally joined at discrete bonds is also stretched effectively as long as there is a difference in bonding strength between the bonds distributed all over and the bonds discretely formed. Examples of the allover joining between layers include adhesion with an adhesive such as a hot-melt adhesive, fusion bonding by the heat of melt at the time of spinning, fusion bonding between fibers and film by heat lamination or hot air application, and fiber entanglement by needle punching or hydroentanglement. The discrete bonds are exemplified by those formed by the above described means including heat embossing, ultrasonic embossing, and an adhesive. Stretching is effected by using the joined sites (bonds) having higher bond strength as starting points of stretching.

When the elastic layer and the substantially inelastic layer are joined all over to each other by, for example, application of a hot-melt adhesive, and the layers are further partially joined at bonds by, for example, heat sealing, the phrase "difference in bond density" means a difference in pattern of joining between the bonds with the hot-melt adhesive and the bonds of the heat sealing. Otherwise, when the allover joining is followed by partial joining, the phrase means a difference in pattern of joining between the allover joining and the partial joining.

The stretch sheet of the invention may have the ridges and grooves as explained with respect to the stretch nonwoven fabric 10 on only one side thereof. While the stretch sheet of the invention has the bonds 4 in the ridges 12, it may have no bonds 4 in the grooves 13. The stretch direction of the stretch sheet may be the width direction of the sheet, perpendicular direction to the machine direction (the running direction of the precursor laminate sheet) or, instead, the longitudinal direction of the sheet. The stretch direction may be at 45 degrees from the width and the longitudinal directions.

Industrial Applicability

According to the processes of the present invention for producing a stretch sheet, a stretch sheet having high stretchability and a good hand and appearance can be produced efficiently.

According to the method of stretching, a laminate sheet or a fibrous sheet can be stretched efficiently in regions other than its bonds or embossed regions without destroying the bonds or embossed regions.

The stretch sheet of the present invention is highly stretchable, bulky, and excellent in cushioning (thickness recovery after compression).

The invention claimed is:

1. A process for producing a stretch sheet comprising:
   passing a laminate sheet through a heat embossing unit, the laminate sheet comprising an elastically stretchable elastic layer and a substantially inelastic fiber layer, and the heat embossing unit forming distinct bond lines each having distinct bonds joining the elastic layer to the inelastic layer; and
   passing the heat embossed laminate sheet between opposing corrugated rolls positioned downstream the embossing unit, the corrugated rolls each having axially alternating large-diameter segments and small-diameter segments in meshing engagement with each other so that large-diameter segments of one corrugated roll fit with clearance between adjacent large-diameter segments of the other corrugated roll, wherein top faces of the large-diameter segments of the corrugated rolls contact at least 40% in number of the distinct bonds during said passing of the laminate sheet between the corrugated rolls so as to positively stretch the laminate sheet starting from said at least 40% in number of the distinct bonds.

2. The process according to claim 1, wherein the laminate sheet is stretched in regions other than the bonds without breaks or separation at the bonds.

3. The process according to claim 1, wherein a pitch of adjacent, meshing, large-diameter segments of opposing corrugated rolls is 2 to 3 times the size of the bonds.

4. The process according to claim 1, wherein top faces of the large-diameter segments of the corrugated rolls contact at least 70% in number of the distinct bonds during said passing of the laminate sheet between the corrugated rolls so as to positively stretch the laminate sheet starting from said at least 70% in number of the distinct bonds.

5. The process according to claim 1, wherein top faces of large-diameter segments of one corrugated roll contact positions of the laminate sheet at every other bond line, and wherein top faces of large-diameter segments of the other corrugated roll contact positions of the laminate sheet at bond lines located between said every other bond line.

6. The process according to claim 1, wherein the laminate sheet is strip-shaped.

7. The process according to claim 1, wherein said stretching is in a width direction of the laminate sheet, a longitudinal direction of the laminate sheet, or at 45 degrees from a width and longitudinal direction of the laminate sheet.

8. The process according to claim 1, wherein said stretching elongates the substantially inelastic fiber layer to cause non-recoverable extension thereof.

9. A process for producing a stretch sheet comprising:
passing a fibrous sheet through a heat embossing unit, the fibrous sheet comprising an elastic component and a substantially inelastic component, and the heat embossing unit forming distinct emboss lines each having distinct embossments; and
passing the heat embossed fibrous sheet between opposing corrugated rolls positioned downstream the embossing unit, the corrugated rolls each having axially alternating large-diameter segments and small-diameter segments in meshing engagement with each other so that large-diameter segments of one corrugated roll fit with clearance between adjacent large-diameter segments of the other corrugated roll,
wherein top faces of the large-diameter segments of the corrugated rolls contact at least 40% in number of the distinct embossments during said passing of the fibrous sheet between the corrugated rolls so as to positively stretch the fibrous sheet starting from said at least 40% in number of the distinct embossments.

10. The process according to claim 9, wherein the fibrous sheet is stretched in regions other than the embossments without breaks or separation at the embossments.

11. The process according to claim 9, wherein a pitch of adjacent, meshing, large-diameter segments of opposing corrugated rolls is 2 to 3 times the size of the embossments.

12. The process according to claim 9, wherein top faces of the large-diameter segments of the corrugated rolls contact at least 70% in number of the distinct embossments during said passing of the fibrous sheet between the corrugated rolls so as to positively stretch the fibrous sheet starting from said at least 70% in number of the distinct embossments.

13. The process according to claim 9, wherein top faces of large-diameter segments of one corrugated roll contact positions of the fibrous sheet at every other emboss line, and wherein top faces of large-diameter segments of the other corrugated roll contact positions of the fibrous sheet at emboss lines located between said every other emboss line.

14. The process according to claim 9, wherein the fibrous sheet is strip-shaped.

15. The process according to claim 9, wherein said stretching is in a width direction of the fibrous sheet, a longitudinal direction of the fibrous sheet, or at 45 degrees from a width and longitudinal direction of the fibrous sheet.

* * * * *